United States Patent [19]
Henley

[11] Patent Number: 5,801,824
[45] Date of Patent: Sep. 1, 1998

[54] LARGE AREA DEFECT MONITOR TOOL FOR MANUFACTURE OF CLEAN SURFACES

[75] Inventor: Francois J. Henley, Los Gatos, Calif.

[73] Assignee: Photon Dynamics, Inc., San Jose, Calif.

[21] Appl. No.: 756,305

[22] Filed: Nov. 25, 1996

[51] Int. Cl.⁶ ................................................. G01N 21/00
[52] U.S. Cl. ........................ 356/237; 356/237; 356/338; 356/339
[58] Field of Search ................... 356/237, 338, 356/339

[56] References Cited

U.S. PATENT DOCUMENTS

| | | |
|---|---|---|
| 3,782,836 | 1/1974 | Fey et al. ............................ 356/209 |
| 4,342,515 | 8/1982 | Akiba et al. ......................... 356/237 |
| 4,377,340 | 3/1983 | Green et al. ......................... 356/237 |
| 4,378,159 | 3/1983 | Galbraith ............................. 356/237 |
| 4,597,665 | 7/1986 | Galbraith et al. ..................... 356/237 |
| 4,597,708 | 7/1986 | Wheeler et al. ...................... 414/331 |
| 4,601,576 | 7/1986 | Galbraith ............................ 356/237 |
| 4,641,967 | 2/1987 | Pecen ................................. 356/237 |
| 4,766,324 | 8/1988 | Saadat et al. ........................ 250/563 |
| 4,772,126 | 9/1988 | Allemand et al. ..................... 356/336 |
| 4,805,123 | 2/1989 | Specht et al. ........................ 364/559 |
| 4,806,774 | 2/1989 | Lin et al. ............................ 250/550 |
| 4,811,409 | 3/1989 | Cavan ................................. 382/358 |
| 4,818,110 | 4/1989 | Davidson ............................. 358/394 |
| 4,845,558 | 7/1989 | Tsai et al. ........................... 356/106 |
| 4,877,326 | 10/1989 | Chadwick et al. ..................... 356/8 |
| 4,895,446 | 1/1990 | Maldari et al. ....................... 356/336 |
| 4,926,489 | 5/1990 | Danielson et al. .................... 382/8 |
| 4,967,095 | 10/1990 | Berger et al. ........................ 250/572 |
| 4,998,019 | 3/1991 | Stokowski .......................... 250/360.1 |
| 5,032,424 | 7/1991 | Vaught .............................. 219/121.6 |
| 5,079,692 | 1/1992 | Neukermans et al. ................. 356/538 |
| 5,083,035 | 1/1992 | Pecen et al. ........................ 250/561 |
| 5,168,386 | 12/1992 | Galbraith .......................... 359/215 |
| 5,172,000 | 12/1992 | Scheff et al. ....................... 250/550 |
| 5,189,481 | 2/1993 | Jann et al. ......................... 356/73 |
| 5,264,912 | 11/1993 | Vaught et al. ...................... 356/237 |
| 5,276,498 | 1/1994 | Galbraith et al. .................... 356/237 |
| 5,317,380 | 5/1994 | Allemand .......................... 356/338 |
| 5,329,351 | 7/1994 | Clementi ........................... 356/237 |
| 5,381,004 | 1/1995 | Uritsky et al. ...................... 250/307 |

OTHER PUBLICATIONS

R. Knollenberg, "A polarization diversity analysis system," *SPIE*, vol. 774, *Lasers in Microlithography*, pp. 32–40 (1987).

*Primary Examiner*—Frank G. Font
*Assistant Examiner*—Reginald A. Ratliff
*Attorney, Agent, or Firm*—Townsend and Townsend and Crew, LLP; Richard T. Ogawa

[57] ABSTRACT

A method and resulting system for directing generally collimated illumination from a source at an oblique angle to a surface under inspection (SUS) to produce scattered nonspecular energy substantially normal to the SUS and for observing the scattered nonspecular energy in one of a plurality of fractional windows of a viewed image of the SUS via a plurality of focussing elements. Such arrangement results in simultaneous and significant throughput and sensitivity enhancement over existing art. The method can be enhanced further wherein the observing step is performed through suitable relative motion of the scattering image over the imaging plane to permit over sampling. Furthermore, the DMT is significantly simplified because imaging is utilized to electronically scan the wafer instead of using opto-mechanical scanning means. Imaging sensors with an aggregate 2000×2000 pixel resolution could image a 200 mm wafer to 100 microns pitch.

26 Claims, 4 Drawing Sheets

LARGE AREA DEFECT MONITOR TOOL FOR MANUFACTURE OF CLEAN SURFACES

BACKGROUND OF THE INVENTION

This invention relates to applications of imaging techniques to inspect for submicron size particles or other artifacts on surfaces, typically planar surfaces under preparation for integrated circuit construction, to determine surface cleanliness. Particulate contamination and defects are a critical problem in the manufacture of integrated circuits.

It is an industry goal to achieve inspection precision with a lower detection limit (LDL) for particles and other defects in a size of about 0.06 microns. Current instruments are capable of particle inspection in the range of 0.1 to 0.08 microns with 95% count efficiency, as determined by standard calibration techniques using polystyrene spheres. Inspection results bettering these accuracy and resolution levels are extremely difficult to achieve because of the barriers of the physical resolution limits of the illumination source and because of the sheer time involved in inspection of all locations on a proportionately large surface.

Using an instrument available for example from KLA Instruments to inspect at 0.1 micron LDL resolution requires on the order of four minutes to inspect a single 200 mm diameter wafer. Inspection at half that LDL may require as much as four times as long, and the optical systems of conventional inspection art simply cannot resolve particles at or below the particle size limit. Long inspection times require that the inspection be made only infrequently and typically independent of the manufacturing process or at least after the completion of many of the processing steps. In fact, inspection times of more than about 45 seconds are considered impractical in the typical cluster tool semiconductor processing system unless some form of queuing is utilized, often making the use impractical. Since a single wafer which is defective may be valued in the tens or hundreds of thousands of dollars, there is a high premium for accurate and rapid inspection.

In order to understand the special problems related to submicron defect measurement, the following information is offered, along with a discussion of known inspection techniques. The following discussion will be focussed on particle detection but the measurement technology can be applied to other surface imperfections such as scratches, digs, etc, and others.

Definitions

The most important specifications describing a particle measurement system are:

1. Throughput

Throughput is the measure of the time taken to scan the wafer at a specified particle size and resolution setting. The environment under which throughput numbers are measured is important. Some coarse detection modes can be much faster than others.

2. Lover Detection Limit

The lower detection limit (LDL) is the minimum detectable particle size which the system can reliably find at different counting efficiencies. This parameter is usually stated for a particular surface (such as a bare silicon wafer) and for PolyStyrene Latex spheres (PSL) particles. This specification is linked to many others, including count repeatability and counting efficiency, and it cannot be specified separately.

3. Counting Efficiency

The counting efficiency is defined as the ratio between the number of particles counted over the total number of particles existing on the wafer. This number will change with a software threshold setting. At sensitive settings, count repeatability will suffer due to the measurement of artifacts of noise as valid particles.

4. Count Repeatability

This value is a relative term quantifying the changes in counting when a wafer is scanned multiple times. It is defined as the ratio between the count standard deviation over the mean number of counts.

5. Particle Sizing Accuracy

How well a particle measurement system can accurately measure a specific particle is also a key specification, but it is one which is often overlooked. Herein it is defined as the percentage departure from the "true" dimension of particles of different size and composition. The error would probably grow worse as the size gets closer to the LDL. There may be other expressions for this specification.

6. Particle Location Accuracy

The system must be able to show the location of the particle it has detected. The location accuracy is herein defined as the +/-3-sigma radius in microns from true particle center. For example, a 3-sigma radius of 50 micron means the location accuracy is +/-50 micron.

7. Layer Ratio

The location ratio is herein defined as the ratio of the LDL of a particle on a bare silicon (Si) wafer to the LDL of the same particle on a particular selected layer. For example, an aluminum (Al) film on silicon (a challenging layer) may have a layer ratio of 0.5, meaning a particle twice the size as one on bare silicon will have the same count efficiency (S/N ratio).

8. Pattern Ratio

The pattern ratio is the ratio of the LDL of bare silicon to the LDL for a particular patterned wafer.

All of the above specifications are highly dependent on the instrument optics, wafer films/patterning/composition, and particle composition. The industry has therefore adopted the use of PSL standards when evaluating and re-certifying a tool.

Conventional Defect Monitor Tool (DMT) Inspection Approaches

The detection and classification of a particle has taken three technology approaches: scatterometric; bright field image processing; and Fourier plane filtering to remove pattern noise. The third approach, one utilized by InSystems (later bought by OAI) is based on pattern noise elimination using Fourier plane filtering. Its use is limited to inspection for defects in spatially repetitive patterns, and its embodiments were costly and bulky. It is noted here because its configurations may look similar to the implementation of the present invention, although there are plainly apparent distinctions. Bright field image processing, as further described hereinafter, is another pattern-based inspection system. It competes with the InSystems approach but is more general due to its ability to inspect both random and repeating patterned wafers. The scatterometric approach will be described in detail in a separate section below.

Scatterometric Particle Measurement Systems

The scatterometric approach for detecting particles uses light scattered from particles which can be collected at many angles from the specular beam. These systems use a dark field scatter measuring method to detect surface anomalies. The dark field method as applied to commercial products can be roughly split into two approaches: scanning beam scatterometric measurement and small area imaging scatterometric systems with mechanical step/repeat systems. Both schemes use a laser point or a collimated beam source impinging on a surface to create scatter off surface artifacts such as particles. Companies utilizing scanning beam scatterometric measurement systems include Tencor, Estek, and Inspex while companies making small area imaging scatterometric systems include Tencor, Insystems/OAI, PMS, and Inspex.

The amount of scatter can be a metric of the particle size. However, the scatter signal is also dependent on particle shape (especially if it is "large"), its reflectance, and dielectric constant and conductivity. FIG. 1 shows a graph of the scattered light intensity as a function of the angle theta for large particles (1), small particles (3), and intermediary sized particles (2). The angle theta ($\theta$) usually denotes the angle between a specular beam and a scattered light of interest. As the angle theta ($\theta$) increases, the scatter efficiency can fall off dramatically with particle having size greater than the measurement light wavelength. The light cross-section fall-off is progressively less severe as the particle size decreases, finally becoming essentially isotropic (equal in all directions) when the particle size is of molecule scale.

FIG. 2 shows the two contributions to a scatter signal: Background and particle scatter. As shown, an incident beam 8 illuminates a spot on a substrate 5 having a particle 4. The scatter signal includes the Background scatter 6, and the particle scatter 7. This figure illustrates that detection sensitivity is dependent on topology (film quality) and patterning. If pattern noise and topological noise have different theta/polarization dependencies from particle scatter, different measurement setups could yield better signal-to-noise ratios and hence more sensitive measurements. Different polarizations and different incidence illumination angles may suppress pattern noise substantially.

A. Scanning beam scatterometric measurement systems

In a laser scanning system, the scattered light is integrated over many practically accessible angles. The system usually scans a wafer by using a CD-type arrangement or a laser scanner. Most present particle detection systems are based on the laser scanning principle. The detection is made via a Photo-Multiplier Tube (PMT). The synchronization of the PMT signal to a laser scan allows a computer to reconstruct a scatter map of the wafer and in turn generate a particle defect map. The Tencor SurfScan laser scanner is an example of this technology.

FIG. 3 shows the conventional approach of the scanning beam scatterometric measurement system 9. The system includes a laser source 10 and a mirror arrangement 111. A wafer 10 is scanned through what is known as an "F-Theta" or other suitable scanning lens arrangement 12 (or through a perpendicular beam with the wafer turned on a platen much like a CD-player). The light is collected at angles 16 away from the specular reflected beam 18 by a Coblenz sphere 20 with a photo-multiplier tube (PMT) 22 serving as a fast and sensitive scatter detector. Most of the light scattered is collected through the sphere arrangement and is usually called a TIS (total integrated scatter) measurement system. The beam is scanned over the wafer while the PMT signal is digitized and accumulated. Passage of the beam over a particle 21 will cause a jump in the measured Background signal 24 because the particle will scatter light at other angles than the reflected beam angle. As shown, the specular beam exists through an opening 19 in the Coblenz sphere.

Laser spot sizes typically range from 40–100 microns. For particle detection specifications of 0.2 microns, the spot is rather large but can still return a clean signal. This means that the Background signal, the signal which is generated from topological (roughness) scatter from the surrounding surface, is smaller than the particle scatter. As rough films are deposited onto the wafer, this background light scatter increases and raises the minimum detectable particle size threshold.

Throughput for such systems seem to require about one minute inspection time for a 200 mm wafer. Although it may be adequate for a process monitor, this throughput cannot be used in-process for wafer-to-wafer particle tracking or integrated into a process tool, since speed is of the essence.

Scanning beam scatterometric measurement systems suffer from the following drawbacks as VLSI becomes ULSI:

The scanning process means that the beam only impinges onto the surface during the brief time it is scanning over it. For a 200 mm wafer and a typical scan beam of 80 microns at 60 seconds total scan time, there is only about 12 microseconds of illumination time for each coordinate.

The brief exposure for each spot means that the photon statistics are low. Therefore, any attempt to increase throughput to allow in-situ measurement further reduces the signal strength to unacceptable levels.

Since the system uses a laser source (usually He-Ne or Ar-ion), there is speckle noise (also called spatial noise) which cannot be averaged or removed. It originates from the locally reproducible but changing speckle pattern integrated over the detector area.

The scanning method is relatively complicated and costly, making an in-situ system bulky and probably too expensive.

The scanning system may not offer very good positioning accuracy: it depends on the use of expensive and complicated optical lenses and designs.

B. Small area imaging scatterometric systems

Another development which occurred which partially resolved some issues of the above scanning systems was to use an area Vidicon or CCD array device 401 with high-magnification optics 402 to measure a relatively small area (about 2–5 mm on a side) 403 and step the area over the entire wafer using mechanical scanning means 404. FIG. 4 illustrates the small area imaging system concept 400. Test times are still in the 60–120 seconds but sensitivity is enhanced through the use of the area imaging device instead of a PMT.

The method used by InSystems to compete with the KLA systems for patterned wafer inspection is a small area imaging scatterometric system using optical Fourier plane pattern elimination. Because the approach uses a large laser and an X-Y scanning subsystem, the system cannot, at first blush, be productized easily into a small package for in-situ integration.

For any small area measurement system, manufacturing cost and complexity will be high since step and repeat mechanisms with high positioning accuracies must be employed. The result is a bulky, low throughput, and high cost per station approach which makes these systems be difficult in integrate in process equipment and other in-situ applications.

Small area imaging scatterometric measurement systems suffer from the following drawbacks as VLSI becomes ULSI:

The small area imaging process means that the area under measurement is only a small part of the whole substrate to be inspected. For a 200 mm wafer and a typical imaging area of 5 mm×5 mm, over 1,200 sites need inspection, requiring fast and expensive stages. Throughput is also limited.

Since the system probably uses a laser source (usually He-Ne or Ar-ion), there is speckle noise (also called spatial noise) which cannot be averaged or removed. It originates from the locally reproducible but changing speckle pattern integrated over the detector area.

The step/repeat method is relatively complicated and costly, making an in-situ system bulky and probably too expensive.

The step/repeat system may not offer very good positioning accuracy: it depends on the use of expensive and complicated mechanical designs.

C. Large area imaging scatterometric systems

A higher throughput, potentially practical DMT concept would be to use simultaneous measurement of a whole surface to negate the need for step/repeat mechanics and increase throughput. Present methods, however, have not been able to achieve whole area imaging at reasonable sensitivities. Resolving this problem and allowing for a practical whole area DMT is the basis of the present invention.

Bright field Image Processing Defect Measurement

Another method to detect particles on a complex surface, such as patterned masks and wafers was pioneered by KLA Instruments, mentioned above. The method uses image processing to eliminate the patterns in a microscope image to yield only the anomalies, which can be particles or missing/extra layer material. The KLA systems are quite expensive (over $1.5–2 million) and large. Full wafer characterization is also slow: a 200 mm wafer can take up to and over 4 minutes to analyze. The tool, however, is quite useful for process control and characterization since it can detect mask problems as well as particles, but it is limited in its applicability as an in-line/in-situ tool.

State Of The Art

Various patents have been uncovered in a search which are useful to understand the state-of-the-art in defect monitoring systems. These patents include:

A. Scanning beam scatterometric measurement systems

1. U.S. Pat. No. 5,317,380 describes a system for minimizing background noise problems related to scattered light in a defect monitor system. This system incorporates a laser scanning system for X-scanning a mechanical translation of the Surface Under Inspection (SUS) for Y-scanning.

2. U.S. Pat. Nos. 4,378,159; 4,597,665; 4,601,576; 4,967,095; 5,076,692; 5,189,481 describe detection improvements to DMT systems, all having some form of laser beam scanning.

3. U.S. Pat. Nos. 4,766,324; 5,329,351 describe thresholding and signal processing methods to increase particle count accuracies.

4. U.S. Pat. No. 5,276,498 describes a method to utilize spatial filters in a scanning system to suppress scattered light of repetitive features of circuit features or the like.

B. Small area imaging scatterometric systems

A good paper explaining the tradeoffs and issues of these DMT systems is "A polarization Diversity Surface Analysis System", Robert G. Knollenberg, SPIE Vol. 774 Lasers in Microlithography (1987). The paper introduces a small area (microscope-based) system with a translation/rotation X-Y scanning arrangement.

1. U.S. Pat. Nos. 4,772,126; 4,806,774; 4,895,446; 5,172,000 describe small area imaging scatterometric systems which either uses polarization/grazing incidence illumination or Fourier plane filtering to suppress scattered light of repetitive features of circuit features or the like.

2. U.S. Pat. No. 5,264,912 describes a system which uses a track filter with slightly incoherent light to allow speckle noise reduction for patterned wafer inspection. Although the surface area was not mentioned, no practical whole area inspection method is mentioned in the patent and a smaller area is assumed. Use of the system for whole substrate inspection would have suffered from the same issues as described in the next section.

C. Large area imaging scatterometric systems

There are no large area imaging scatterometric systems on the market today, but the basic though impractical idea was described in at least one patent. The inventors of this patent actually are largely the same as a series of subsequent patents mentioned above (A-1 and B-1) where this first idea of whole substrate inspection was apparently abandoned in preference to scanning and small area scatterometric systems.

1. U.S. Pat. No. 4,377,340 describes a system which may image a whole wafer but with very low light collection efficiencies. Reported sensitivities were 0.3 micron and 0.1 micron was mentioned as theoretically possible. The patent also described the use of an image intensified camera to detect these particles. Since these cameras are known to be noisy, the problem of light collection efficiency must be resolved to allow practical whole substrate inspection. This patent will be further discussed in the next sections.

D. Bright field Image Processing Defect Measurement

For completeness, bright field image processing defect measurement will be included, although its use in whole wafer measurement is not considered practical or cost effective.

1. U.S. Pat. Nos. 4,845,558; 4,877,326 describe substrate inspection using bright field image processing using a small area, X-Y stage scanned inspection method.

Limitations of Conventional Techniques and Goal of the Present Invention

Referring to FIG. 3, there is shown a conventional scanning scatterometric detector 8 as described above. This design approach was cost effective in the early/mid-1980s for particle size measurement of 0.2 micron and above and for off-line use. It has, however, been experiencing severe limitations as substrate sizes increase and LDL specs requirements have decreased. These systems are no longer cost effective for in-situ measurement and cannot achieve measurement times of less than 45 seconds or so.

Referring to FIG. 4, there is shown a conventional small area imaging scatterometric system 400 as described above. Although the system can achieve lower LDLs due to the use of new CCD imaging devices, the mechanical step and repeat and the sequential measurement method will limit the LDL. The throughput will not be significantly improved over the older scanning systems. To be practically integrated into a cluster tool processing system, both the measurement head cost and the throughput would have to be significantly improved.

Referring to FIG. 5, there is shown a conventional large area imaging scatterometric system 500 as described above. The system utilizes a highly sensitive image intensified camera 501 viewing a portion of the whole wafer 503 (up to 6 inch wafer sizes were discussed). The need for a high sensitivity camera is obvious from the required optical arrangement. Using a standard ½ inch vidicon, a demagnification factor of 22 is necessary to test modern 200 mm diameter silicon substrates. Using the f/4 camera lens 502 as discussed in the patent, the resulting f-number at the substrate would be f/88. This very large f-number means that little light is being collected by the camera, thereby requiring the aforementioned image intensifier. Going to lower image f-numbers is possible (such as f/1 or f/2 but the substrate f-number would be 20–40, still too large for practical systems. Lower lens f-numbers would increase cost dramatically and cause other artifacts such as aberrations.

Since the system LDL roughly scales as particle diameter to the fourth power ($D^4$), this arrangement is not only challenged at 0.3 micron particle sizes but will not scale well to lower particle diameters (a 0.1 micron particle is 81 times weaker in scatter cross-section). The problem cannot be resolved by increasing camera gain further, since noise will be amplified in the same proportion to the particle signal. Photon noise will dominate in this regime of operation, and only by increasing signal statistics (by integrating more light) will the noise be proportionally lower than the signal. It is therefore increasingly difficult using the conventional embodiment to simultaneously measure larger substrate diameters while increasing the system sensitivity to achieve lower LDLs.

This issue is the basic problem with the conventional of large area imaging scatterometric systems and probably caused the inventors to abandon this approach and adopt scanning and small area imaging. The problem was severe in 1982 and only worsened for modern DMT requirements.

Therefore the goal of the present invention is to resolve the above technical barriers to allow large area imaging scatterometric systems to accurately and rapidly test and thus insure the integrity of this class of flat surfaces with high sensitivity and throughput.

SUMMARY OF THE INVENTION

According to the present invention, a defect monitoring tool is provided wherein generally collimated illumination is directed from a source to a SUS and then resultant scattered nonspecular energy of all points in a window of a viewed image of the SUS is simultaneously observed at a remote focal plane via light collecting elements. Multiple lenses/camera detectors are utilized to inspect the whole substrate surface simultaneously with significantly better light collection efficiencies as was possible using the conventional techniques. Camera detectors may be used to inspect the scatter-energy image projected on the focal plane.

In a specific embodiment, the DMT is significantly simplified because imaging is utilized to electronically scan the wafer instead of using opto-mechanical scanning means. Imaging sensors with an aggregate 2000×2000 pixel resolution could image a 200 mm wafer to 100 microns pitch. This is roughly equal the performance of a laser scanner with an 80 microns laser spot size. After detection of the scattered light across the substrate, image processing methods are used to take all intermediate images and assemble a defect file corrected for location and overlap. Because the measurement head is now simplified by eliminating any opto-mechanical scanning, multiple measuring heads to a single computer/image processing platform could substantially lower the effective measuring cost to the user.

An alternative specific embodiment provides a method for observing defects on a surface by means of optically scattered energy. The present method includes steps of directing generally collimated illumination from a source at an oblique angle to a surface under inspection to produce scattered nonspecular energy substantially normal to the SUS. A step of observing the scattered nonspecular energy in one of a plurality of fractional windows of a viewed image of the SUS via a plurality of focussing elements at a plurality of remote focal planes having a symmetrical detection arrangement is also provided. The focal planes are mounted adjacent one another and arranged in a symmetrical array arrangement adjacent one another. The symmetrical detection arrangement corresponds to the symmetrical array arrangement.

In a modification to the preceding embodiment, the observing step occurs without relative motion between the symmetrical detection arrangement and the symmetrical array arrangement to permit over sampling. Alternatively, the observing step occurs without relative motion between the SUS and the symmetrical detection arrangement to permit oversampling. Alternatively, the observing step is performed without relative motion between the SUS and the symmetrical detection arrangement to permit oversampling.

A further specific embodiment includes a system for observing defects on a surface by means of optically scatter energy. The present system includes means for directing generally collimated illumination from a source at an oblique angle to a surface under inspection (SUS) to produce scattered nonspecular energy substantially normal to the SUS. The present system also includes a means for observing the scattered nonspecular energy in one of a plurality of fractional windows of a viewed image of the SUS via a plurality of focussing elements at a plurality of remote focal plans having a symmetrical detection arrangement. The focal plans are mounted adjacent one another and arranged in a symmetrical array arrangement adjacent one another. The symmetrical detection arrangement corresponds to the symmetrical array arrangement.

The present invention as described herein resolves such limitations and other limitations of the aforementioned conventional systems.

Photon Dynamics, Inc. the assignee of the present invention, has developed a number of imaging systems, instruments and tools for non-contact testing of flat panel displays and the like. To this end it has developed an expertise in transferring images to electronic inspection devices and in software for analyzing large amounts of arrayed information efficiently. This expertise has lead the inventor to resolve the major barriers keeping large area imaging scatterometric systems from becoming practical.

The present invention will be better understood by reference to the following detailed description in connection with accompanying drawings.

DESCRIPTION OF SPECIFIC EMBODIMENTS

The present invention allows high light collection efficiencies to be achieved in a large area imaging scatterometric system which in turn allows significantly better LDLs to be achieved with high throughput.

For best sensitivity and noise performance, a CCD array allowing at least 50,000–100,000 electron per pixel charge integration is necessary to get good statistics. Devices with high resolution (1000×1000 or higher) are now available and could be used in this application. The present invention allows sufficient light collection efficiencies to reach the aforementioned charge integration levels for maximum measurement sensitivity.

Figure 6:
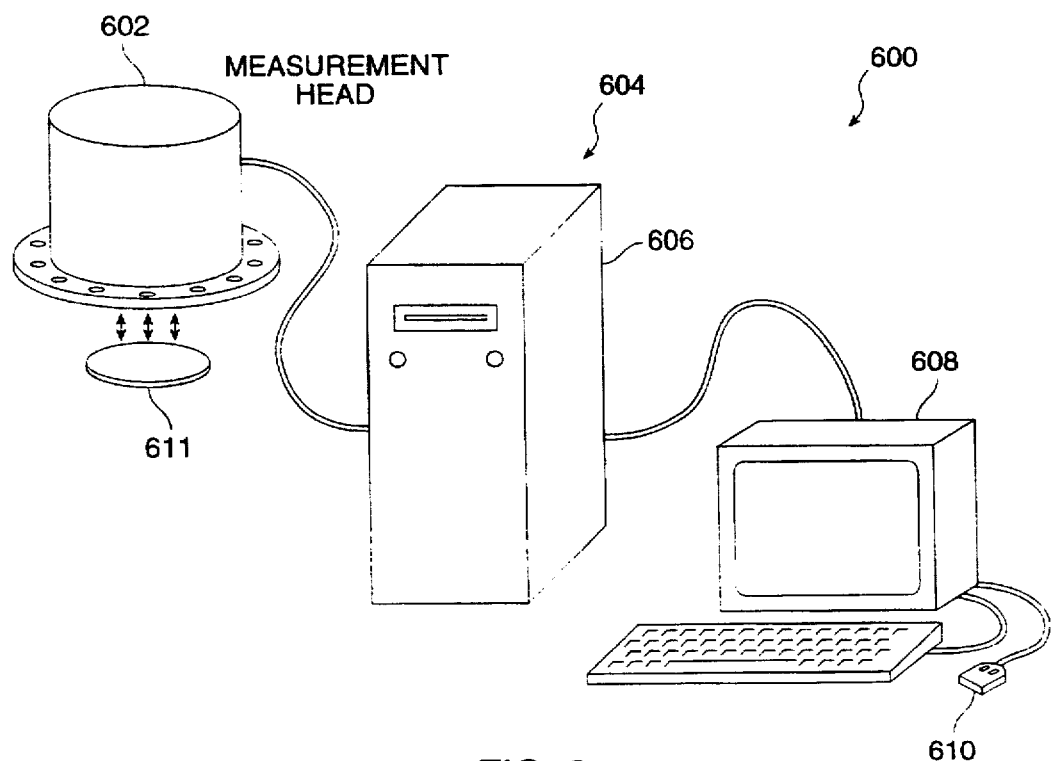
FIG. 6 is an illustration of a system according to the present invention.

FIG. 6 shows a simplified outside view of the present measurement DMT system 600 as currently conceived. The measurement optical subsystem 602 is attached, preferably bolted, onto a cluster tool and is roughly about 0.7 meter in length or less to measure the whole area of a substrate 611, such as a 200 mm and greater silicon wafer. The signals are connected to a SUN VME-based SPARC system 604 or any other suitable system with an image processor 606, a monitor 608, and a keyboard/mouse 610. For automatic operation, the system is controlled via SECS, Ethernet, RS-232, or another.

Figure 7:
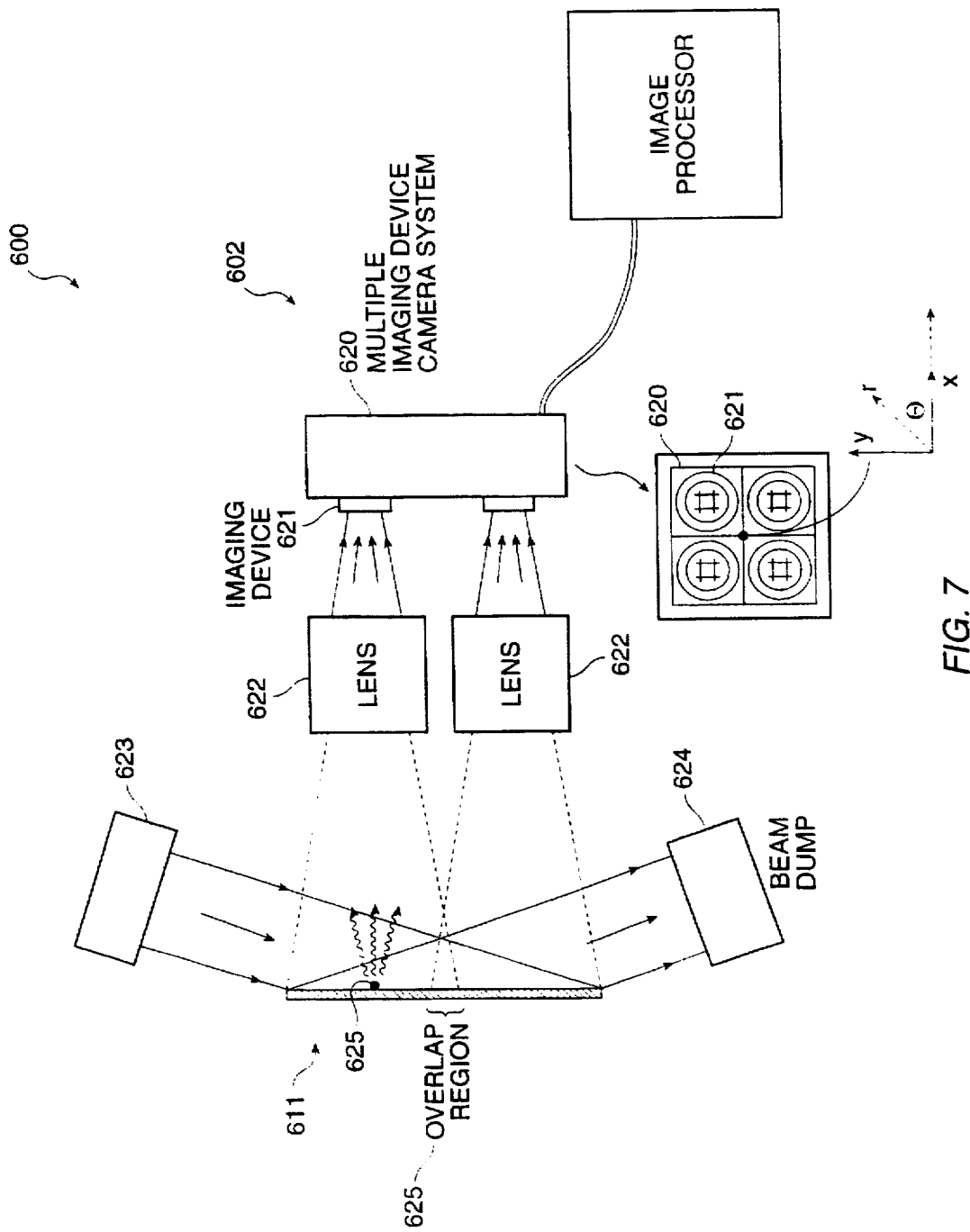
FIG. 7 is a block diagram of a large area scatter detector according to the present invention.

FIG. 7 shows a simplified design of the DMT system measurement head 602, according to the present invention. The DMT system 600 includes at least an illuminator 623 and beam dump 624, an array of CCD imaging devices 621 and corresponding camera electronics 620, a wafer 611, measurement lenses 622, a particle 625, among other elements. The system shows a 2×2 camera design 620 using corresponding 2×2 CCD tandem electronics design. The 2×2 camera design is of Cartesian symmetry. Alternatively, the camera design may be of Polar symmetry or any other type of symmetry suitable for the particular application. The CCD camera elements may be any high quality CCD-type cameras such as a Kodak MegaPlus 1.6, which can allow frame integration. Each of the four CCD imaging arrays 621 (1×1 k each) receives a 7.5× demagnified image from 100 mm to roughly 14 mm using a f/1.4 to f/1.0 high quality but commercially available camera lens 622. This type of pixel array configuration may scan a spot size on the wafer of about 100×100 microns. Alternatively, the f-number is f/1.5 or f/0.9, and the lens is operative at an effective object f-number of less than f/20. Preferably, the effective object f-number is f/9 and less.

Figure 1:
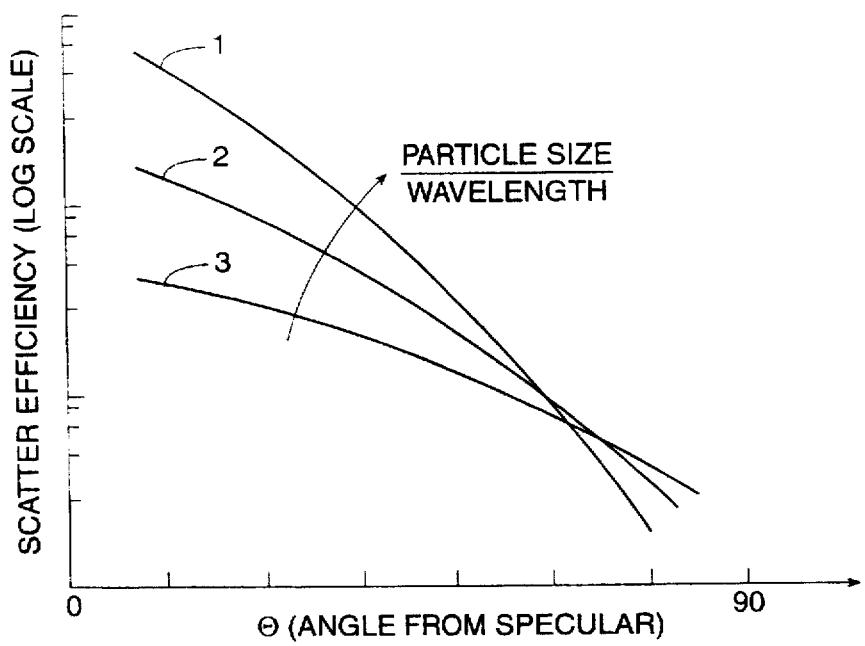
FIG. 1 is a graph of the scattering cross-section of particles of different size/wavelength ratios.
Figure 2:
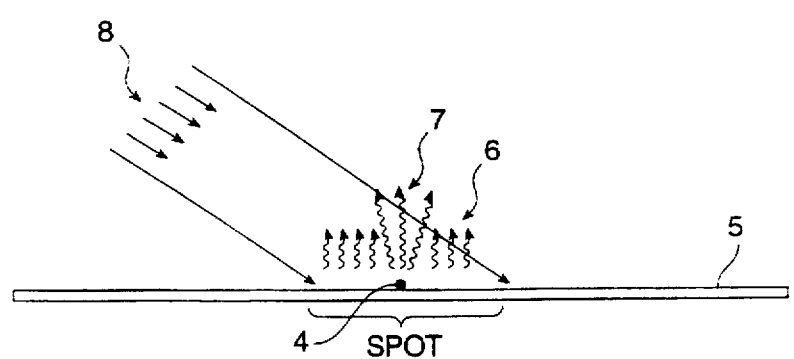
FIG. 2 is a schematic illustration of background and particle signal.
Figure 3:
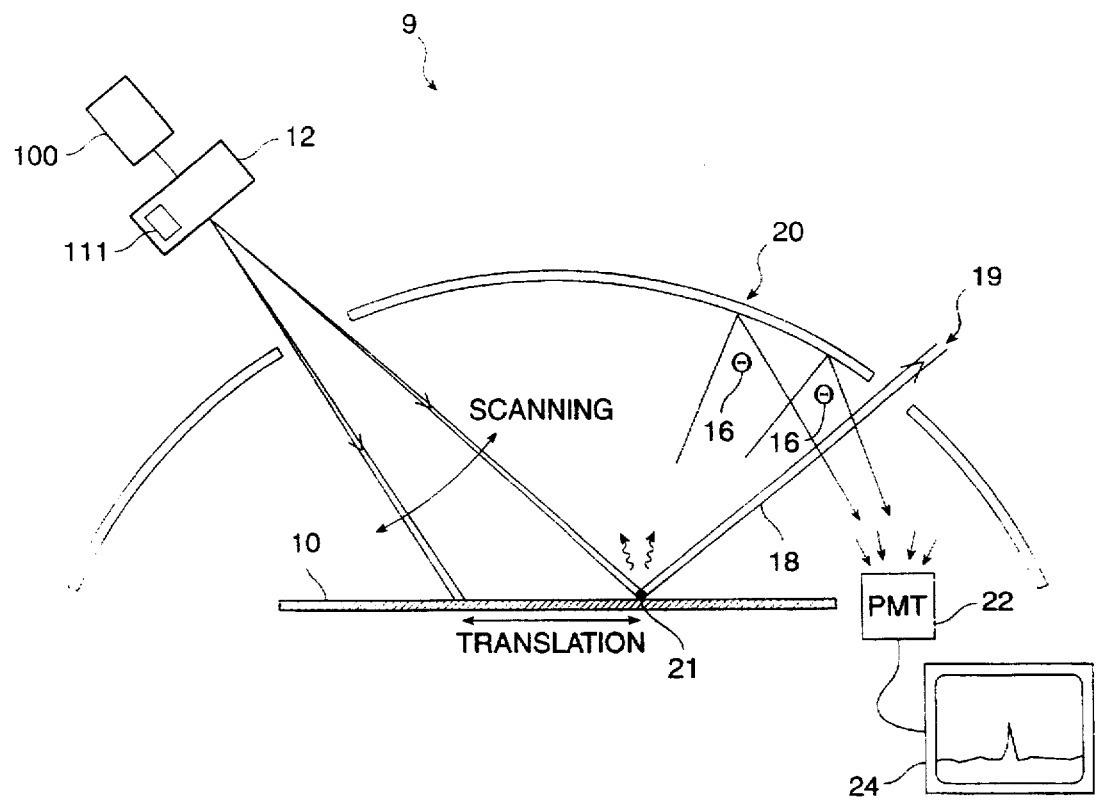
FIG. 3 is a schematic illustration of a conventional scanning scatterometric system.
Figure 4:
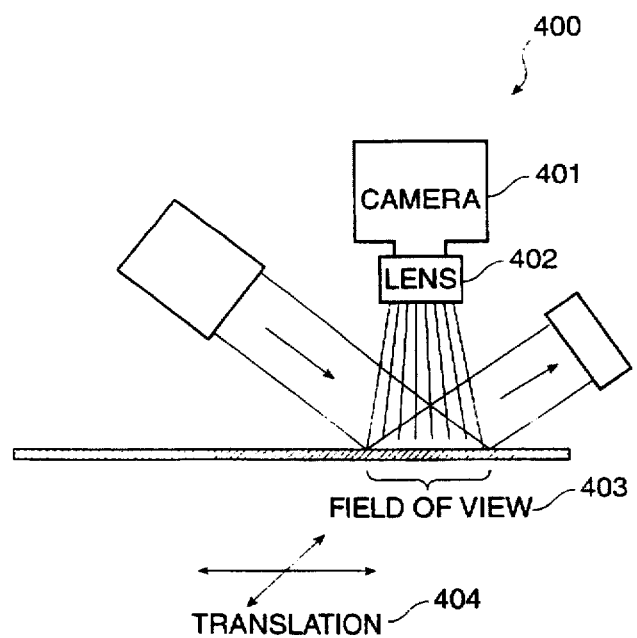
FIG. 4 is a schematic of a conventional small area imaging scatterometric system.
Figure 5:
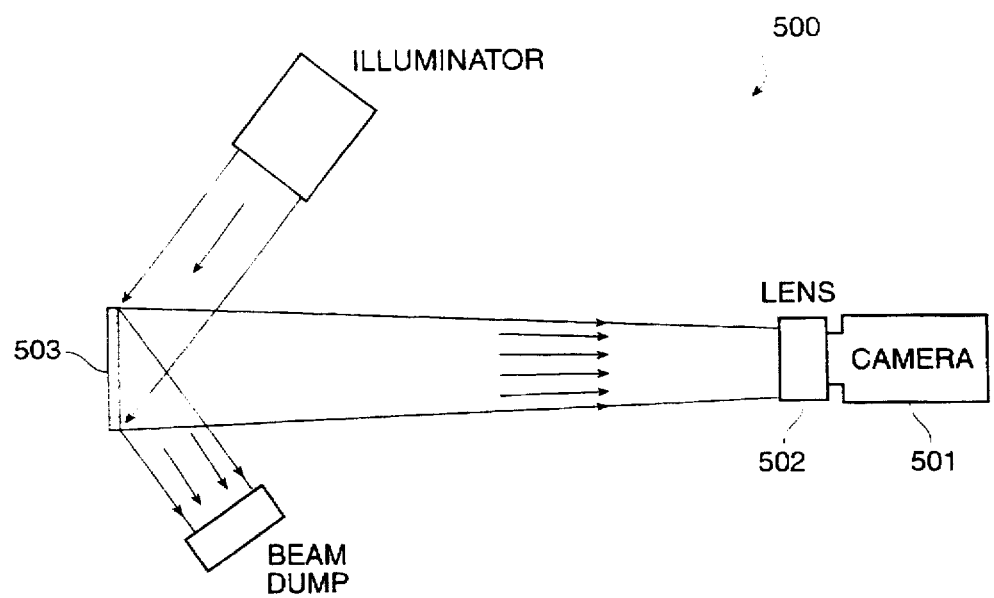
FIG. 5 is a schematic of a conventional large area imaging scatterometric system.

Of course, as technology progresses, larger pixel arrays such as 2×2 k and greater may be used to scan a substrate with even higher resolution. If a smaller area on the wafer is mapped onto each CCD pixel, the resulting signal is lower in noise due to a smaller integration of background signal as previously noted by way of FIG. 2.

The light originates from a spectrally filtered source 623 such as an arc-lamp with cutoff filters or any other suitable light source. The desired light may be in the range of 475 nm to 750 nm but may be narrower to simplify the optics design. The illumination occurs from the side via a suitably filtered high intensity line source. The high angle of illumination would guarantee dark field and remove any scatter specification issue from lenses 622 since the illumination beam is not coincident with the collection optics. The reflected specular beam would then be dumped on the other side of the illuminator via a suitably designed beam dump 624.

The four images are preferably taken simultaneously, thereby preserving the feature of non-mechanical sampling of the whole wafer. The images will be transferred and reassembled by the camera electronics 620 and a computer/image processor 606 to yield a processed image which shows the defect "size" and location corrected for all intra and inter-lens distortions and inaccuracies. The overlap area 625 will also be corrected in the image processor by using multiple defect removal from the overlap areas of each camera image using prior knowledge of the extent and location of the overlap areas. More processing, possibly using signature analysis software, could take this defect information to further collapse the information to yield process deficiencies.

The CCD array may be placed on an X-Y stage (not shown) for location accuracy enhancement through oversampling. Of course, the type of X-Y stage depends upon the particular application.

The DMT system 600 is illustrated with a sample wafer 611 which may be monitored for particles and the like. The DMT system may be incorporated on-line (or in-line) by the aforementioned bolt-on technique onto the cluster tool or any other suitable means. This will provide an in-situ monitoring tool to detect particles on for example the wafer. As an insitu monitoring tool, no particles are introduced onto the sample wafer in transit between a particular process and the DMT system. In addition, scattering caused by air will often be insignificant in the cluster tool, which is generally at a vacuum and lacks air.

Alternatively, the DMT system 600 may also be an off-line monitoring tool. As an off-line monitoring tool, it can provide quick and accurate particle counts on a sample wafer. However, particles can be introduced onto the sample wafer while being transported from the particular process to the off-line monitoring tool. Of course, the preferred embodiment will be the in-situ version of the DMT system, rather than the off-line version.

In both off-line and in-line embodiments, the present system also benefits from a cost advantage over the conventional techniques in that the majority of the system cost reside in the computer/image processing system 604, while the measurement head 602 is relatively inexpensive due to its electronic scanning nature. Since a computer/image processing system 604 could in principle control and support multiple measurement heads, the resulting cost per station (measurement head) would be smaller than any conventional approach using expensive step/repeat and scanning technologies.

In an embodiment, the DMT systems of FIGS. 6–7 may be set-up with the following features with use of a bare silicon wafer. Throughput at selected sensitivities range from about 1 to about 3 seconds capture, and even less. A LDL for the bare silicon wafer is less than about 0.1 micron, and preferably less than about 0.06 micron or about 0.07 micron or about 0.08 micron. A count repeatability may range from about 80% to about 95%, and is preferably at about 95% and greater. A rough estimate of achievable Particle Location Accuracy is less than about 1 CCD pixel or about 100 microns.

Each configuration of the DMT systems of FIGS. 6–7 provide improved features to the aforementioned conventional systems. For example, the present DMT systems include a "single-shot" approach to the measurement of particles on the wafer with enhanced signal to noise ratios. These features provide massively reduced test times with greater sensitivity to lower particle sizes. In addition, the present DMT systems do not "scan" across the wafer surfaces as some conventional systems, thereby reducing and possibly eliminating any scanning noise and light source fluctuations. Furthermore, the present DMT systems may be incorporated into a cluster tool which is under a vacuum, and will therefore reduce or possibly eliminate air scatter contributions and provide in-situ processing. These features of the present DMT system provide benefits that simply cannot be obtained by way of the aforementioned conventional systems.

The present invention has now been explained with reference to specific embodiments. Other embodiments will be apparent to those of ordinary skill in the art. It is therefore not intended that the present invention be limited except as indicated by the appended claims.

What is claimed is:

1. A display fabrication method comprising a method for observing defects on a surface by optically scattered energy, the method for observing comprising:

providing a portion of a display device, said portion comprising a surface under inspection (SUS);

directing generally collimated illumination from a source at an angle to said SUS to produce scattered nonspecular energy substantially normal to said SUS; and observing said scattered nonspecular energy in one of a plurality of fractional windows of a viewed image of the SUS via a plurality of focussing elements at a plurality of remote focal planes having a detection arrangement, said focal planes being mounted adjacent one another arranged in an array arrangement adjacent one another, said detection arrangement corresponding to said array arrangement;

wherein said observing and directing steps occur simultaneously and are performed substantially without any relative motion between said SUS and said detection arrangement to substantially reduce a possibility of any scanning noise and light source fluctuations.

2. The method according to claim 1 wherein said detection arrangement and said array arrangement are of symmetry.

3. The method according to claim 1 wherein said detection arrangement and said array arrangement are of Polar symmetry.

4. The method according to claim 1 wherein said focal planes are in an imaging array of an electronic camera.

5. The method according to claim 1 wherein said focal planes are an imaging surface, said imaging surface being operative to convert said nonspecular energy into detectable energy.

6. The method according to claim 1 wherein each of said focusing elements is a high-quality lens having an f-number of about f/1.5 and less.

7. The method according to claim 1 wherein each of said focusing elements is a high-quality lens operative at an effective object f-number of less than f/20, said high-quality lens being a refractor.

8. The method according to claim 7 wherein each of said focussing elements is operative at an effective object f-number of less than f/9, said refractor having a minimum f-number of smaller than f/1.5 and greater than f/0.9.

9. The method according to claim 1 wherein said source emits in narrow wavelength range of noncoherent light.

10. The method according to claim 1 wherein said collimated illumination is spectrally filtered noncoherent light.

11. The method according to claim 1 wherein said collimated illumination is coherent light.

12. The method according to claim 1 wherein said observing step is performed without relative motion between said detection arrangement and said array arrangement to permit over sampling.

13. The method according to claim 1 wherein said observing step is performed without relative motion between said SUS and said array arrangement to permit over sampling.

14. The method according to claim 1 wherein said observing step is performed without relative motion between said SUS and said detection arrangement to permit over sampling.

15. An apparatus for observing optically scattered energy from a surface by means of optically scattered energy, the apparatus comprising:

a light source for directing generally collimated illumination from a source at an angle to a surface under inspection (SUS) to produce scattered nonspecular energy substantially normal to said SUS; and a plurality of electronic cameras for observing said scattered nonspecular energy in one of a plurality of fractional windows of a viewed image of the SUS via a plurality of focussing elements at a plurality of remote focal planes having a detection arrangement, said focal planes being mounted adjacent one another arranged in an array arrangement adjacent one another, said detection arrangement corresponding to said array arrangement, said SUS and said array arrangement having substantially no relative motion between said SUS and said array arrangement to substantially reduce a possibility of any scanning noise and light source fluctuations.

16. The apparatus according to claim 15 wherein said detection arrangement and said array arrangement are of Cartesian symmetry.

17. The apparatus according to claim 15 wherein said detection arrangement and said array arrangement are of Polar symmetry.

18. The apparatus according to claim 15 wherein said focal plane is in an imaging array of an electronic camera.

19. The apparatus according to claim 15 wherein said focal plane is an imaging surface, said imaging surface being operative to convert said nonspecular energy into detectable energy.

20. The apparatus according to claim 15 wherein each of said focusing elements is a high-quality lens having an f-number of about f/1.5 and less.

21. The apparatus according to claim 15 wherein each of said focusing elements is a high-quality lens operative at an effective object f-number of less than f/20, said high-quality lens being a refractor.

22. The apparatus according to 21 wherein each of said focussing elements is operative at an effective object f-number of less than f/9, said refractor having a minimum f-number of smaller than f/1.5 and greater than f/0.9.

23. The apparatus according to claim 15 wherein said source emits in narrow wavelength range of noncoherent light.

24. The apparatus according to claim 15 wherein said collimated illumination is spectrally filtered noncoherent light.

25. The apparatus according to claim 15 wherein said collimated illumination is coherent light.

26. The apparatus according to claim 15 is in communication with a cluster tool semiconductor processing system.

* * * * *